United States Patent
Zopf et al.

(10) Patent No.: US 11,458,012 B2
(45) Date of Patent: Oct. 4, 2022

(54) SCAFFOLD FOR NASAL TISSUE ENGINEERING

(71) Applicants: THE REGENTS OF THE UNIVERSITY OF MICHIGAN, Ann Arbor, MI (US); GEORGIA TECH RESEARCH CORPORATION, Atlanta, GA (US)

(72) Inventors: David Zopf, Ann Arbor, MI (US); Scott J. Hollister, Atlanta, GA (US)

(73) Assignees: THE REGENTS OF THE UNIVERSITY OF MICHIGAN, Ann Arbor, MI (US); Georgia Tech Research Corporation, Atlanta, GA (US)

( * ) Notice: Subject to any disclaimer, the term of this patent is extended or adjusted under 35 U.S.C. 154(b) by 0 days.

(21) Appl. No.: 16/434,500

(22) Filed: Jun. 7, 2019

(65) Prior Publication Data
US 2019/0374336 A1 Dec. 12, 2019

Related U.S. Application Data (60) Provisional application No. 62/681,811, filed on Jun. 7, 2018.

(51) Int. Cl.
*A61F 2/18* (2006.01)
*A61L 27/18* (2006.01)
(Continued)

(52) U.S. Cl.
CPC .............. *A61F 2/186* (2013.01); *A61L 27/18* (2013.01); *A61L 27/3839* (2013.01);
(Continued)

(58) Field of Classification Search
CPC .............. A61F 2/186; A61F 2250/0067; A61F 2002/0081; A61F 2240/002; A61F 2/18;
(Continued)

(56) References Cited

U.S. PATENT DOCUMENTS

| 4,595,713 A | 6/1986 | St. John |
| 5,433,748 A | 7/1995 | Wellisz |

(Continued)

FOREIGN PATENT DOCUMENTS

| CN | 203183985 U | 9/2013 |
| CN | 104783922 A | 7/2015 |

(Continued)

OTHER PUBLICATIONS

Zopf et al (David A. Zopf, Anna G. Mitsak, Colleen L. Flanagan, Matthew Wheeler, Glenn E. Green and Scott J. Hollister "Computer Aided-Designed, 3-Dimensionally Printed Porous Tissue Bioscaffolds for Craniofacial Soft Tissue Reconstruction": Otolaryngology—Head and Neck Surgery, Oct. 3, 2014) (Year: 2014).*

(Continued)

*Primary Examiner* — Brian A Dukert
*Assistant Examiner* — Rebecca Lynee Zimmerman
(74) *Attorney, Agent, or Firm* — Harness, Dickey & Pierce, P.L.C.

(57) ABSTRACT

A nasal tissue implant for reconstruction and tissue engineering of nasal tissue in a subject includes a tissue scaffold component comprising a biocompatible polymeric material having a plurality of open pores configured to support cell growth. The tissue scaffold component conforms to a portion of the subject's nasal region and defines at least a portion of the subject's nasal anatomy. A method of making an implantable nasal tissue implant for reconstructing a portion of a nasal anatomy of a human or other animal subject is also provided that includes laser sintering or three-dimensional (Continued)

(3D) printing a biocompatible polymeric material to form a tissue scaffold component comprising a biocompatible polymeric material having a plurality of open pores configured to support cell growth. Again, the tissue scaffold component substantially conforms to a nasal region specific to the human or other animal subject.

20 Claims, 4 Drawing Sheets

(51) Int. Cl.
  *A61L 27/38* (2006.01)
  *A61M 27/00* (2006.01)
  *A61L 27/56* (2006.01)
  *A61F 2/00* (2006.01)

(52) U.S. Cl.
  CPC ............ *A61L 27/56* (2013.01); *A61M 27/00* (2013.01); *A61F 2002/0081* (2013.01); *A61F 2240/002* (2013.01); *A61F 2250/0067* (2013.01)

(58) Field of Classification Search
  CPC ...... A61L 27/18; A61L 27/3839; A61L 27/56; A61L 2430/06; A61M 27/00; B33Y 80/00
  See application file for complete search history.

(56) References Cited

U.S. PATENT DOCUMENTS

| | | | |
|---|---|---|---|
| 6,187,329 | B1 | 2/2001 | Agrawal et al. |
| 6,454,803 | B1 | 9/2002 | Romo, III |
| 8,071,007 | B1 | 12/2011 | Teoh et al. |
| 8,480,737 | B2 | 7/2013 | Hristov et al. |
| 9,180,029 | B2 | 11/2015 | Hollister et al. |
| 9,510,940 | B2 | 12/2016 | Chen et al. |
| 9,949,823 | B2 | 4/2018 | Hristov et al. |
| 10,149,753 | B2 | 12/2018 | Chen et al. |
| 10,213,296 | B2 | 2/2019 | Shim |
| 11,071,623 | B2 | 7/2021 | Rosenthal et al. |
| 2005/0113918 | A1 | 5/2005 | Messerli et al. |
| 2010/0023130 | A1 | 1/2010 | Henry et al. |
| 2010/0168856 | A1 | 7/2010 | Long et al. |
| 2010/0204793 | A1 | 8/2010 | Byrd et al. |
| 2010/0292641 | A1 | 11/2010 | Wijay et al. |
| 2011/0264236 | A1 | 10/2011 | Bassett et al. |
| 2014/0364946 | A1 | 12/2014 | Chen |
| 2016/0015502 | A1 | 1/2016 | Noble |
| 2016/0200043 | A1 | 7/2016 | Thian et al. |
| 2018/0055643 | A1* | 3/2018 | Castro ............... A61L 27/48 |
| 2020/0188090 | A1 | 6/2020 | Zopf et al. |

FOREIGN PATENT DOCUMENTS

| | | |
|---|---|---|
| CN | 205264210 U | 5/2016 |
| DE | 4006145 A1 | 8/1990 |
| DE | 3943201 A1 | 7/1991 |
| KR | 102061194 B1 | 2/2020 |
| WO | 2016038083 A1 | 3/2016 |
| WO | 2018167292 A1 | 9/2018 |
| WO | 2018200816 A1 | 11/2018 |

OTHER PUBLICATIONS

Correa, Bryan. J. et al., "The Forehead Flap: The Gold Standard of Nasal Soft Tissue Reconstruction," Seminars in Plastic Surgery (2013), 27 (2), pp. 96-103; DOI:10.1055/s-0033-1351231.

Immerman, Sara et al., "Cartilage Grafting in Nasal Reconstruction," Facial Plastic Surgery Clinics of North America, vol. 19, Issue 1, (2011) pp. 175-182; DOI: 10.1016/j.fsc.2010.10.006.

International Search Report and Written Opinion for International Application No. PCT/US2018/029575 dated Aug. 17, 2018 (ISA/KR), 12 pages.

Cervantes, Thomas M. et al., "Design of composite scaffodls and three-dimensional shape analysis for tissue-engineered ear," J. R. Soc. Interface 10, Apr. 13, 2013 (Published online Jun. 10, 2013); DOI: 10.1098/rsif.2013.0413.

Hollister, Scott J. et al., "Design Control for Clinical Translation of 3D Printed Modular Scaffolds," Annals of Biomedical Engineering 43(3) (Published online Feb. 10, 2015); DOI: 10.1007/s10439-015-1270-2.

Partee, Brock et al., "Selective Laser Sintering Process Optimization for Layered Manufacturing of CAPA® 6501 Polycaprolactone Bone Tissue Engineering Scaffolds," J. Manuf. Sci E. 128, pp. 531-540 (May 2006); DOI: 10.1115/1.2162589.

Zopf, David et al., "Biomechanical Evaluation of Human and Porcine Auricular Cartilage," The Laryngoscope 125, pp. E262-E268 (Publsihed Apr. 17, 2015); DOI: 10.1002/lary.25040.

Zopf, David et al., "Computer-Aided, 3-Dimensionally Printed Porous Tissue Bioscaffolds for Craniofacial Soft Tissue Reconstruction," Otolaryngology—Head and Neck Surgery (2015), vol. 152(1), pp. 57-62; DOI: 10.1177/0194899814552065.

Extended European Search Report for European Patent Application No. 18789867.1 dated Dec. 14, 2020, 8 pages.

* cited by examiner

SCAFFOLD FOR NASAL TISSUE ENGINEERING

CROSS-REFERENCE TO RELATED APPLICATIONS

This application claims the benefit of U.S. Provisional Application No. 62/681,811, filed on Jun. 7, 2018. The entire disclosure of the above application is incorporated herein by reference.

FIELD

The present disclosure relates to tissue engineering with a nasal tissue scaffold for partial or full reconstructing of a nasal region specific to the human or other animal subject, where the nasal tissue scaffold can be formed via additive manufacturing.

BACKGROUND

This section provides background information related to the present disclosure which is not necessarily prior art.

Nasal reconstruction has unique challenges for providing both structurally functional and aesthetic end results. Disfigurement from trauma, resection of malignancy, and rarely congenital deformity or absence of nasal structure can lead to the need for significant surgical intervention to regain function and aesthetics of the nose. When there are larger defects impacting the skin and cartilage of the nose, a staged paramedian forehead flap process is performed (Correa, et al., 2013). For total nasal reconstruction, costal cartilage as the basis for an L-strut with additional cartilage, such as conchal, for further structural composition is often utilized (Immerman, et al., 2011). In the elderly population, costal cartilage is frequently ossified, adding greater challenges for harvesting and manipulation. The need for high volumes of donor cartilage and significant difficulty in precisely replicating the complex structure of the native nasal tripod pose vast challenges for the nasal reconstructive surgeon. It would be desirable to have a tissue scaffold component for tissue engineering that enables more facile and accurate reconstruction of a defect in a nasal region specific to the human or other animal subject.

DRAWINGS

The drawings described herein are for illustrative purposes only of selected embodiments and not all possible implementations, and are not intended to limit the scope of the present disclosure.

FIGS. 1A-1D depict nose skin contact analysis.

FIGS. 2A-2B show an anatomic based total nasal bioscaffold design.

FIGS. 3A-3H show a nasal cartilage tissue engineering scaffold prepared in accordance with certain aspects of the present disclosure being surgically implanted in a cadaver to demonstrate aesthetics and more specifically, a prelaminated forehead flap, pericranial flap with use of a 3D-printed total nasal bioscaffold. Preprocedural photodocumentation of nasal structure, right lateral (FIG. 3A) and basal view (FIG. 3B). FIG. 3C is a right lateral view showing a total nasal defect. FIG. 3D shows in situ placement of a 3D-printed total nasal bioscaffold prepared in accordance with certain aspects of the present disclosure. A prelaminated 3D-printed bioscaffold implanted in a forehead flap is shown in FIG. 3E. FIG. 3F shows subsequent elevation of underlying pericranial flap providing an internal mucosal lining. FIGS. 3G and 3H show the completed inferior rotation and inset of a total nasal graft using the 3D-printed total nasal bioscaffold with overlying paramedian forehead flap and pericranial internal lining, basal view (FIG. 3G) and right lateral view (FIG. 3H).

FIGS. 4A-4D show a process of creating and implanting an anatomical based nasal cartilage tissue engineering scaffold.

FIGS. 5A-5B depict computer rendered anatomical-based models of two nasal bioscaffold embodiments. In FIG. 5A, the implant includes large pores with tissue punch biopsies inserted therein. In FIG. 5B, the implant includes a combination of small pores and large pores with tissue punch biopsies inserted into the large pores.

Corresponding reference numerals indicate corresponding parts throughout the several views of the drawings.

DETAILED DESCRIPTION

Example embodiments are provided so that this disclosure will be thorough, and will fully convey the scope to those who are skilled in the art. Numerous specific details are set forth such as examples of specific compositions, components, devices, and methods, to provide a thorough understanding of embodiments of the present disclosure. It will be apparent to those skilled in the art that specific details need not be employed, that example embodiments may be embodied in many different forms and that neither should be construed to limit the scope of the disclosure. In some example embodiments, well-known processes, well-known device structures, and well-known technologies are not described in detail.

The terminology used herein is for the purpose of describing particular example embodiments only and is not intended to be limiting. As used herein, the singular forms "a," "an," and "the" may be intended to include the plural forms as well, unless the context clearly indicates otherwise. The terms "comprises," "comprising," "including," and "having," are inclusive and therefore specify the presence of stated features, elements, compositions, steps, integers, operations, and/or components, but do not preclude the presence or addition of one or more other features, integers, steps, operations, elements, components, and/or groups thereof. Although the open-ended term "comprising," is to be understood as a non-restrictive term used to describe and claim various embodiments set forth herein, in certain aspects, the term may alternatively be understood to instead be a more limiting and restrictive term, such as "consisting of" or "consisting essentially of." Thus, for any given embodiment reciting compositions, materials, components, elements, features, integers, operations, and/or process steps, the present disclosure also specifically includes embodiments consisting of, or consisting essentially of, such recited compositions, materials, components, elements, features, integers, operations, and/or process steps. In the case of "consisting of," the alternative embodiment excludes any additional compositions, materials, components, elements, features, integers, operations, and/or process steps, while in the case of "consisting essentially of," any additional compositions, materials, components, elements, features, integers, operations, and/or process steps that materially affect the basic and novel characteristics are excluded from such an embodiment, but any compositions, materials, components, elements, features, integers, operations, and/or process steps that do not materially affect the basic and novel characteristics can be included in the embodiment.

Any method steps, processes, and operations described herein are not to be construed as necessarily requiring their performance in the particular order discussed or illustrated, unless specifically identified as an order of performance. It is also to be understood that additional or alternative steps may be employed, unless otherwise indicated.

When a component, element, or layer is referred to as being "on," "engaged to," "connected to," or "coupled to" another element or layer, it may be directly on, engaged, connected or coupled to the other component, element, or layer, or intervening elements or layers may be present. In contrast, when an element is referred to as being "directly on," "directly engaged to," "directly connected to," or "directly coupled to" another element or layer, there may be no intervening elements or layers present. Other words used to describe the relationship between elements should be interpreted in a like fashion (e.g., "between" versus "directly between," "adjacent" versus "directly adjacent," etc.). As used herein, the term "and/or" includes any and all combinations of one or more of the associated listed items.

Although the terms first, second, third, etc. may be used herein to describe various steps, elements, components, regions, layers and/or sections, these steps, elements, components, regions, layers and/or sections should not be limited by these terms, unless otherwise indicated. These terms may be only used to distinguish one step, element, component, region, layer or section from another step, element, component, region, layer or section. Terms such as "first," "second," and other numerical terms when used herein do not imply a sequence or order unless clearly indicated by the context. Thus, a first step, element, component, region, layer or section discussed below could be termed a second step, element, component, region, layer or section without departing from the teachings of the example embodiments.

Spatially or temporally relative terms, such as "before," "after," "inner," "outer," "beneath," "below," "lower," "above," "upper," and the like, may be used herein for ease of description to describe one element or feature's relationship to another element(s) or feature(s) as illustrated in the figures. Spatially or temporally relative terms may be intended to encompass different orientations of the device or system in use or operation in addition to the orientation depicted in the figures.

Throughout this disclosure, the numerical values represent approximate measures or limits to ranges to encompass minor deviations from the given values and embodiments having about the value mentioned as well as those having exactly the value mentioned. Other than in the working examples provided at the end of the detailed description, all numerical values of parameters (e.g., of quantities or conditions) in this specification, including the appended claims, are to be understood as being modified in all instances by the term "about" whether or not "about" actually appears before the numerical value. "About" indicates that the stated numerical value allows some slight imprecision (with some approach to exactness in the value; approximately or reasonably close to the value; nearly). If the imprecision provided by "about" is not otherwise understood in the art with this ordinary meaning, then "about" as used herein indicates at least variations that may arise from ordinary methods of measuring and using such parameters. For example, "about" may comprise a variation of less than or equal to 5%, optionally less than or equal to 4%, optionally less than or equal to 3%, optionally less than or equal to 2%, optionally less than or equal to 1%, optionally less than or equal to 0.5%, and in certain aspects, optionally less than or equal to 0.1%.

In addition, disclosure of ranges includes disclosure of all values and further divided ranges within the entire range, including endpoints and sub-ranges given for the ranges.

Example embodiments will now be described more fully with reference to the accompanying drawings.

The present disclosure contemplates a nasal implant and more specifically, a nasal tissue scaffold implant for partial or full reconstruction by tissue engineering of a portion of a nasal region or nose in a subject having a defect in the nasal region or nose. In certain aspects, a nasal tissue scaffold includes a tissue scaffold component comprising a biocompatible polymeric material having a plurality of open pores configured to support cell growth. The tissue scaffold component may conform to a portion of the subject's nasal region and further defines at least a portion of the subject's nasal anatomy, for example, a portion of the subject's nose or nasal cavity. In certain variations, one or more portions or all of the nasal tissue scaffold may be solid and lack pores depending on desired adjacent soft tissue interactions, for example. The nasal tissue scaffold can promote regrowth of tissue to create and reconstruct the portion of the subject's nasal anatomy where the defect was present. It should be noted that the nasal tissue scaffold implant may also be used to create and/or conform to other craniofacial regions of the subject when the defect is larger and extends beyond the nasal region, for example, into the malar or cheek regions. In certain aspects, a tissue scaffold may comprises one or more relatively large openings that may be considered large diameter pores that receive a tissue sample, such as a punch biopsy of tissue that promotes regrowth.

In various aspects, the present disclosure provides nasal implant devices for reconstructing tissue in a patient or subject. The subject may be an animal, such as a mammal, including a human. The reconstructed tissue may be nasal tissue, including cartilage. In various aspects, the nasal implant includes a tissue scaffold component that promotes cell ingrowth. Thus, a tissue scaffold component comprises a plurality of open pores configured to support cell growth. In various aspects, the tissue scaffold component comprises a first biocompatible polymeric material. Specific materials to be used in the implant devices of the present technology that are biocompatible are preferably biomedically acceptable. Such a "biomedically acceptable" material is one that is suitable for use with humans and/or animals without undue adverse side effects (such as toxicity, irritation, and allergic response) commensurate with a reasonable benefit/risk ratio. In certain variations, the biocompatible polymeric material may be a composite material having a reinforcement phase or material distributed therein.

In certain embodiments, the nasal implant devices of the present technology comprise a biocompatible polymer, such as a biodegradable polymer. The biocompatible polymeric material may comprise a biocompatible or biomedically acceptable polymer. The biocompatible polymer may be biodegradable or non-biodegradable. The term "biodegradable" as used herein means that the implant comprising the polymer is slowly dissolved or disintegrated under physiological conditions in the human or other animal subject for a certain time and at some point only its degradation products are present in the body in a dissolved or comminuted form. At this point, solid components or fragments of the implant either do not exist anymore or are so small as to be non-harmful or transported away by the subject's circulatory system. The degradation products are desirably substantially harmless in physiological terms and lead to molecules that either occur naturally in the human or other animal subject or can be excreted by the human or other animal subject.

Biodegradable polymers include polycaprolactone, polysebacic acid, poly(octaindiolcitrate), polydioxanone, polygluconate, poly(lactic acid) polyethylene oxide copolymer, modified cellulose, polyhydroxybutyrate, polyamino acids, polyphosphate ester, polyvalerolactone, poly-6-decalactone, polylactonic acid, polyglycolic acid, polylactides, polyglycolides, copolymers of the polylactides and polyglycolides, polyhydroxybutyric acid, polyhydroxybutyrates, polyhydroxyvalerates, polyhydroxybutyrate-co-valerate, poly(1,4-dioxane-2,3 one), poly(1,3-dioxane-2-one), poly-para-dioxanone, polyanhydrides, polymaleic acid anhydrides, polyhydroxy methacrylates, fibrin, polycyanoacrylate, polycaprolactone dimethylacrylates, poly-3-maleic acid, polycaprolactone butyl acrylates, multiblock polymers from oligocaprolactonediols and oligodioxanonediols, polyether ester multiblock polymers from PEG and poly(butylene terephthalates), polypivotolactones, polyglycolic acid trimethyl carbonates, polycaprolactone glycolides, poly(methyl glutamate), poly (DTH-iminocarbonate), poly(DTE-co-DT-carbonate), poly(bisphenol A-iminocarbonate), polyorthoesters, polyglycolic acid trimethyl carbonate, polytrimethyl carbonates, polyiminocarbonates, poly(N-vinyl)-pyrrolidone, polyvinyl alcohols, polyester amides, glycolized polyesters, polyphosphoesters, polyphosphazenes, poly[p-(carboxyphenoxy) propane], polyhydroxy pentanoic acid, polyanhydrides, polyethylene oxide propylene oxide, and combinations thereof. In various embodiments, a preferred biodegradable biocompatible polymer that forms the nasal implant device comprises, or consists essentially of, polycaprolactone.

In various embodiments, the nasal implant device comprising the biodegradable biocompatible polymer allows the nasal tissue to grow over and into the tissue scaffold and heal naturally. The implant may then biodegrade or resorb in the subject or patient. Having the implant biodegrade will not inhibit regrowth in adults or growth in children. In various embodiments, the nasal implant device is designed to have a degradation time that coincides with the healing time that permits regrowth of the defect in the patient. "Degradation time" refers to the time for the nasal implant device implanted to substantially and fully dissolve, disintegrate, or resorb. Depending upon the patient and the time needed for recuperation and regeneration of the nasal tissue, the degradation time may be about 3 weeks to about 60 months (5 years), or about 2 months to about 40 months (3.33 years), or about 6 months to about 36 months (3 years), or about 12 months to about 24 months (2 years). As noted above, in certain embodiments, a preferred biodegradable biocompatible polymer used to form the nasal implant device comprises polycaprolactone, which desirably enables a degradation time of 6 months to about 36 months (3 years) under normal physiological conditions when implanted in an animal subject/patient.

The term "non-biodegradable polymer" as used herein means that the biocompatible or biomedically acceptable polymer forming the implant will not dissolve in the human or animal subject. These polymers do not substantially resorb, dissolve or otherwise degrade after implantation in a human or animal subject, under typical physiological conditions.

In certain embodiments, the nasal implant device of the present disclosure optionally comprises a non-biodegradable biocompatible polymer. Suitable biomedically acceptable non-biodegradable biocompatible polymers include polyaryl ether ketone (PAEK) polymers (such as polyetherketoneketone (PEKK), polyetheretherketone (PEEK), and polyetherketoneetherketoneketone (PEKEKK)), polyolefins (such as ultra-high molecular weight polyethylene, which may be crosslinked, and fluorinated polyolefins such as polytetrafluorethylene (PTFE) or high density porous polyethylene), polyesters, polyimides, polyamides, polyacrylates (such as polymethylmethacrylate (PMMA)), polyketones, polyetherimide, polysulfone, polyurethanes, and polyphenolsulfones. The nasal implant device may comprise multiple biocompatible polymers, including one or more biodegradable biocompatible polymers, one or more non-biodegradable biocompatible polymers, and any combinations thereof. Thus, in certain variations, a portion of the nasal implant device may be biodegradable, while another portion of the implant is a permanent and non-biodegradable.

The nasal implant device of the present technology can further comprise one or more bioactive materials. More specifically, the first biocompatible polymeric material and the second biocompatible polymeric material may independently comprise a bioactive material. Depending on such factors as the bioactive material, the structure of the nasal implant device, and the intended use of the implantable nasal reconstruction device, the bioactive material may be coated on a surface of the tissue scaffold component, coated or otherwise infused in the pores or openings of the tissue scaffold component, or mixed or compounded within the biocompatible polymeric material of the nasal implant device.

Bioactive materials can include any natural, recombinant or synthetic compound or composition that provides a local or systemic therapeutic benefit. In various embodiments, the bioactive material promotes healing and growth of a nasal tissue resulting from a defect, including congenital defects or injuries or wounds resulting from trauma or surgery (such as oncologic surgical intervention). Bioactive materials among those useful herein include cell adhesion factors, isolated tissue materials, growth factors, peptides and other cytokines and hormones, pharmaceutical actives, nanoparticles, and combinations thereof. Cell adhesion factors include, for example, the RGD (Arg-Gly-Asp) sequence or the IKVAV (Ile-Lys-Val-Ala-Val) sequence. Growth factors and cytokines useful herein include transforming growth factor-beta (TGF-β), including the five different subtypes (TGF-β 1-5); bone morphogenetic factors (BMPs, such as BMP-2, BMP-2a, BMP-4, BMP-5, BMP-6, BMP-7 and BMP-8); platelet-derived growth factors (PDGFs); insulin-like growth factors (e.g., IGF I and II); fibroblast growth factors (FGFs), vascular endothelial growth factor (VEGF), epidermal growth factor (EGF) and combinations thereof. Examples of pharmaceutical actives include antimicrobials, antifungals, chemotherapeutic agents, and anti-inflammatories. Examples of antimicrobials include triclosan, sulfonamides, furans, macrolides, quinolones, tetracyclines, vancomycin, cephalosporins, rifampins, aminoglycosides (such as tobramycin and gentamicin), and mixtures thereof.

In certain variations, a nasal implant device comprises a bioactive material in the form of a biomaterial that may be selected from the group consisting of: an isolated tissue material, a hydrogel, acellularized dermis, an acellularized tissue matrix, a composite of acellularized dermis matrix and designed polymer, or a composite of acellularized tissue matrix and designed polymer, and combinations thereof. An isolated tissue material may include an autologous or allogeneic tissue sample (such as an explant harvested in the patient by a punch biopsy to provide tissue sample). In other aspects, an isolated tissue material may include isolated or cultured cells (such as chondrocyte cells, hemopoietic stem cells, mesenchymal stem cells, such as adipose-derived mesenchymal stem cells, endothelial progenitor cells, fibroblasts, reticulacytes, and endothelial cells), whole blood and blood fractions (such as red blood cells, white blood cells, platelet-rich plasma, and platelet-poor plasma), collagen, fibrin, acellularized dermis, and the like. In one embodiment, the isolated tissue biomaterial may comprise a combination of porcine adipose-derived stem cells and/or bone marrow derived or induced pluoripotent stem cells with chondrocytes, which may be combined at ratios of about 1:1 to 10:1. Hydrogels are materials formed from lightly-cross-linked networks of natural or synthetic polymers, such as saccharides, which have high water contents such as 90% weight per volume or greater. Hydrogel crosslinking can be achieved by various methods including ionic, covalent chemical, or UV-initiated chemical crosslinking. Hydrogels used in the present disclosure are preferably biocompatible. Hydrogels may be formed from hyaluronic acid/hyaluronan, sodium alginate, polyethylene glycol (PEG), polyethylene glycol diacrylate (PEGDA), 2-hydroxyethyl methacrylate (HEMA)/poly(2-hydroxyethyl methacrylate) (pHEMA), polymethyl methacrylate (PMMA), polyacrylic acid, chitosan, poly(amino acids), poly(N-isopropylacrylamide) (PNI-PAM), collagen, gelatin, fibronectin, chondroitin sulfate, surfactant gels (having greater than about 20% weight per volume poloxamers (e.g., commercially available as PLURONIC™ and BRU™), polydimethylsiloxane (PDMS) or dimethicone, epoxy, polyurethane, and the like. In one embodiment, a suitable hydrogel based biomaterial may comprise hyaluronic acid and Type I collagen. In certain aspects, an implantable nasal device may have a biomaterial disposed on one or more surfaces that will contact tissue in the patient upon implantation of the nasal implant device.

In certain aspects, the biocompatible polymeric material comprises a biodegradable polymer.

In certain aspects, the biocompatible and biodegradable polymeric material of the nasal implant comprises polycaprolactone.

In certain aspects, the biocompatible polymeric material further comprises a bioactive agent selected from the group consisting of: a cell adhesion factor, a growth factor, a peptide, a cytokine, a hormone, a pharmaceutical active, and combinations thereof.

In certain aspects, the biocompatible polymeric material further comprises a biomaterial. The biomaterials may be selected from the group consisting of: an isolated tissue material, a hydrogel, acellularized dermis, an acellularized tissue matrix, a composite of acellularized dermis matrix and designed polymer, or a composite of acellularized tissue matrix and designed polymer, and combinations thereof.

In certain aspects, the biocompatible polymeric material comprises a material selected from the group consisting of: nanoparticles, growth factors, cells, tissue infusions, and combinations thereof.

The present disclosure thus contemplates scaffold based tissue engineering for nasal reconstruction. The nasal implant assembly to be implanted on or in a patient may be selected from prefabricated implant devices having common sizes and dimensions or may be customized to a patient by using an image-based design approach to tailor the design to a specific human or animal subject. Where the nasal implant device is manufactured for a specific patient, it provides a personalized, customizable solution for several possible applications in nasal reconstruction, including reconstruction of a congenital deformity, reconstruction in oncologic resection, and reconstruction in trauma or blast injury, by way of example. Such techniques provide the ability to incorporate age, gender, and ethnic specific properties to these nasal implant devices. The image-based design approach uses medical images or other data that is specific to the subject to customize the size of the nasal implant device. Scaffold implants can be produced from extrapolation of nasal defects or virtual repair of congenital malformations. Also, mirrored scaffolds allow perfect symmetry in repair for each side of the nose, when required.

The present disclosure thus contemplates scaffold based tissue engineering for nasal reconstruction. The nasal tissue scaffold implant may be implanted in or attached to a subject in a nasal region and thus may conform to at least a portion of the nasal region. In certain aspects, the present disclosure contemplates a method of making an implantable nasal tissue implant for reconstructing a portion of a nasal anatomy of a human or other animal subject. The method may comprise laser sintering or three-dimensional (3D) printing via an additive manufacturing process a biocompatible polymeric material to form a tissue scaffold component comprising a biocompatible polymeric material having a plurality of open pores configured to support cell growth. The tissue scaffold component substantially conforms to a nasal region specific to the human or other animal subject.

In certain other aspects, the method may further comprise designing a tissue scaffold component from a set of medical image data of the nasal region specific to the human or other animal subject prior to the laser sintering or three-dimensional (3D) printing. In certain variations, specific medical images and/or parameters are obtained from one or more imaging systems such as computed tomography (CT), a CT-fluoroscopy, fluoroscopy, magnetic resonance imaging (MRI), ultrasound, positron emission tomography (PET) and X-Ray systems or any other suitable imaging systems. In certain aspects, a nasal implant scaffold may be produced from a laser or light 3D scan, multipod photography, or pre-existing CT/MRI scan of the patient.

The medical image data and/or parameters received from the imaging system provide a two-dimensional (2D), three-dimensional (3D) or four-dimensional (4D) model of an anatomical structure, system or region of the patient, here the nasal region of the patient. The image-based design of the 2D, 3D or 4D model may be created using MATLAB®, Mathematica®, or other computer-aided-designed (CAD)

software design programs known in the art. For converting the design into a usable format for rapid prototyping and computer-aided manufacturing, a STL file format may be created. This file format is supported by many software packages such as Mimics® by Materialise, MATLAB®, IDL, and Amira®. More specifically, Digital Imaging and Communications in Medicine (DICOM) data is shown for the anatomic structure of interest (e.g., a nasal region) of a subject and used to generate a three-dimensional model of the structure.

This 2D, 3D or 4D model of the nasal implant device of the present technology may then be used to manufacture the nasal tissue scaffold implant device. The implant device may be made by a variety of suitable methods, including methods comprising solid free-form fabrication (SFF) techniques, such as laser sintering, stereolithography, 3D printing, injection molding and the like. In various embodiments, the preferred method is an additive manufacturing process of laser sintering. Laser sintering is a process involving the construction of a three-dimensional article by selectively projecting a laser beam having the desired energy onto a layer of particles of the polymer material to be sintered. The laser sintering process can be paired with medical image data and/or parameters received from the imaging system for producing a customized nasal implant device of the present technology. The model is thus converted into a porous structure using negative Boolean operations and manufactured from polycaprolactone using an additive manufacturing process, such as selective laser sintering three-dimensional (3D) printer.

Next, the pores of the bioresorbable scaffold may be seeded with a bioactive materials, such as cells suspended in a hyaluronic acid/collagen hydrogel prior to implantation. In this manner, the present disclosure contemplates forming mirrored tissue scaffolds allowing perfect symmetry in repair for each side of the nose. Such techniques can produce patient specific anatomic soft tissue implants and tissue engineering scaffolds that can reproduce complex craniofacial structures with high fidelity.

In certain variations, Computer Aided Design (CAD) and 3D printing is thus utilized to form a nasal tissue scaffold implant. Such an implant or device provides a personalized, customizable solution for several possible applications in nasal reconstruction. This tissue scaffold implant represents multiple novel features for partial and total nasal cartilage tissue scaffolds designed to allow for unparalleled ease in translation and for wide dissemination as well as use in remote surgical settings such as medical mission work.

Three-dimensional (3D) printing provides the opportunity for patient-specific, anatomic based design and manufacturing solutions for nasal reconstruction. In addition, new materials are enabling 3D printing to be safe, biocompatible, and anatomically accurate. This disclosure presents a novel, 3D-printed bioscaffold innovation and proposed technique for total nasal reconstruction that may dramatically enhance reproducible and pleasing aesthetic outcomes and dramatically reduce operative time and demands.

The development of this novel, 3D-printed nasal bioscaffold provides a promising answer to the challenges presented by traditional total nasal reconstruction methods. The scaffold-to-skin contact analysis demonstrates a significantly larger strain on the scaffold protuberances, indicating ideal locations for the placement of patient-specific cartilage cells obtained through punch biopsies. These high stress locations promote cell proliferation and differentiation to populate the nose scaffold with the patient's own cartilage cells. The scaffold to skin contact analysis can be a numerical finite element analysis performed using software, such as FEBio, that simulates the skin as a nonlinear elastic material and the scaffold as a linear elastic material. In certain variations, based on such an FEA analysis, the implant may include relative large pores for receiving punch biopsy tissue inserts in strategic locations. By using such a model, areas of high strain are identified in the overlapping skin regions reflecting where the skin is more likely to breakdown, ulcerate and where the scaffold/implant may potentially extrude. Thus, the scaffolds can be designed to receive tissue inserts within those high stress locations. Generally, the locations of these high stress points generally tend to occur in the same areas on patients, but may shift due to individual anatomy and therefore may require personalization of the large diameter holes that receive tissue inserts in the manufactured implant to correspond to the specific anatomic locations of a given patient. For example, these anatomic areas are commonly the tip defining regions of the nasal tip, delineated by the intermediate crura of the lower lateral cartilages and the nasal dorsum, comprised of the septal cartilage/bone and upper lateral cartilages. It is believed that these whole nose implants will resist the deformation seen in other bioscaffolds due to material fracture, extrusion, or infection.

The additive manufacturing of this scaffold allows for more patient-specific total nasal reconstruction, considering the patient's gender, race, and aesthetic preferences. An expert surgeon can reconstruct a well-sculpted nose over multiple surgical stages requiring cartilage harvest. However, results from this procedure can be highly variable, even with a highly skilled practitioner. Use of the scaffold implants prepared in accordance with certain aspects of the present disclosure can reduce the number of required surgeries, limit the amount of rib cartilage harvested, and dramatically reduce intraoperative time.

The techniques and scaffold design provided by the present teachings provide the capability for immediate translation and wide clinical use. By employing CAD and 3D printing, while integrating foundational surgical techniques, a surgical device and technique that may transform total nasal reconstruction.

Image based CAD processes allow customized patient specific scaffolds with one or more of the following advantages: mirrored scaffolds allowing high levels of symmetry in repair, scaffolds produced from extrapolation of nasal defects, scaffolds produced from a laser 3D scan, multipod photography, or pre-existing CT/MRI scan, refined tripod scaffolds produced from algorithm based on normative data based on human nasal tripod dissection; and ability to incorporate age, gender, and ethnic specific properties to these scaffolds.

Tailored scaffold porosity provides a capability of hybrid or gradated scaffold pores. Pore placement can form a scaffold having strength and rigidity at foundational subunits (septum, dorsum, columnella), while porous architecture imparts flexibility at subunits adjacent to soft tissue interfaces (tip defining points of the nasal tip, alar wings). As such, the size and/or density of pores may be smaller or less at regions of the implant corresponding to foundational subunits so as to achieve a stiffer material and the pores may be larger or there is a higher pore density at subunits adjacent to soft tissue interfaces to provide greater flexibility in those region. Thus the porous scaffold may have more pores in areas where greater flexibility is required and fewer pores in areas where greater stiffness is required. In certain variations, porosity imparts gradated permeability with high internal permeability, low peripheral permeability allowing low impedance, high homogeneity with various biomaterials, such as hydrogel, solution, nanoparticle, growth factor, cell, tissue infusion or combinations thereof.

Furthermore, partial scaffolds may be designed based on prior surgical expertise and normative data for: medial, intermediate, or lateral crura; alar wings; partial or total nasal tip complex; spreader grafts; butterfly grafts; L-strut including and in isolation, dorsum, tip complex, columnella, upper lateral cartilages, batton supports, lateral crural supports, and any combination thereof. Certain embodiments aim to optimize internal and/or external nasal valves, mechanisms encouraging open internal and external nasal valves, and/or custom composite scaffolds based on patient specific defect need.

Figure 5A:
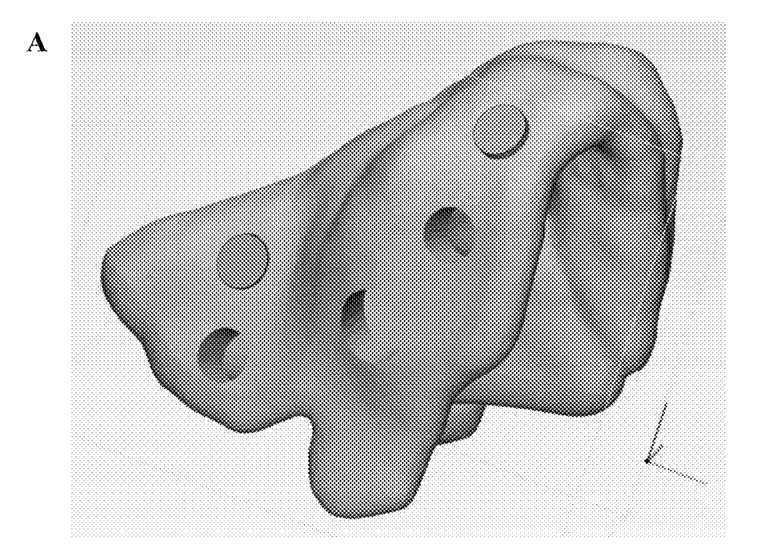
Figure 5B:
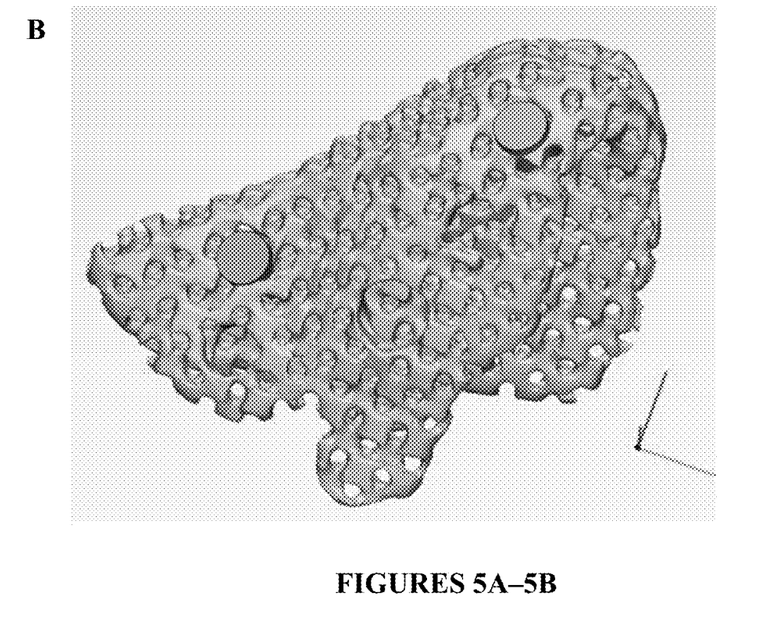

In other aspects, prefabricated punch biopsy inserts can be employed with the nasal tissue scaffold implants, as shown for example, in FIGS. 5A-5B. The size and distribution of cartilage punch biopsy inserts based on Finite Element Analysis guides relief of overlying soft tissue strain and vascular compromise. Punch tissue insets may be designed with back stop rim or ledge preventing displacement within the nasal cavity during implantation and introduction of the tissue insert. In another variation, prefabricated inserts are offset, so as to allow the cartilage to protrude from an exposed surface of the tissue implant at a range of greater than or equal to about 50 micrometers to less than or equal to about 10 mm, based on Finite Element Analysis guiding relief of overlying soft tissue strain and vascular compromise. Further, porous scaffold designs may radiate from prefabricated punch biopsy inserts facilitating cellular and paracrine dissemination. Additionally, custom punch biopsy designs and accompanying scaffold inserts, e.g., semilunar, elliptical, patient/anatomy specific punch biopsy designs allow rapid and precise harvest and scaffold distribution. An eluting periinsert component allows gradual dissolution of the cartilage punch, further facilitating cellular outgrowth and paracrine influence.

In certain embodiments employing prefabricated punch biopsy inserts, the nasal tissue scaffold implants comprise a plurality of relatively large sized open pores having an average diameter sized and configured to receive biopsy tissue inserts. In certain variations, the average diameter of the plurality of pores may be greater than or equal to about 1 mm to less than or equal to about 10 mm. The biopsy tissue inserts may serve as the primary source of cells, as in the embodiment depicted in FIG. 5A. Further, the large pores or openings may be designed as suture holes for securing the implant during implantation. Additionally or alternatively, the nasal tissue scaffold implants of certain embodiments may be formed having a plurality of relatively large pores for receiving the biopsy inserts and a plurality of relatively smaller pores. Thus, the nasal tissue scaffold implants optionally comprise a first plurality of first open pores having a first average diameter and a second plurality of second open pores having a distinct second average diameter. The first average diameter is greater than the second average diameter. In this manner, the nasal tissue scaffold implant includes a plurality of relatively large pores for receiving the biopsy tissue inserts. In certain variations, the first average diameter of the first plurality of first pores may be greater than or equal to about 1 mm to less than or equal to about 10 mm and the second average diameter of the second plurality of second pores may be greater than or equal to about 0.05 mm to less than or equal to about 2 mm. In such embodiments, the tissue biopsy inserts placed in the relatively large first pores may serve as one source of cells and cell seeding onto the scaffold with native tissue ingrowth into the smaller second pores may serve as another source of cells. Advantageously, in some embodiments, the presence of punch tissue biopsy inserts within the nasal tissue scaffold implant enables cushioning by providing a softer interaction with skin and may reduce strain concentrations in the overlying skin.

The present disclosure also contemplates scaffolds facilitating modular mechanisms, including multistage surgery modular scaffold designs.

Example embodiments include superficial nasal components upper lateral cartilages, dorsum, nasal tip complex, lower lateral cartilages, columnella or any combination thereof included in the first stage module scaffold, which may be subsequently elevated and supported by a second stage septal support.

In certain aspects, the nasal tissue implant design allows a locking mechanism upon coapting modules, for example, a dove tail or offset snap design. In such a variation, the nasal tissue implant comprises two or more components or modules that may be joined together, for example, during implantation or to provide capability for multiple stages of implantation. Inert silicone place holders in the first stage scaffold may provide a fresh edge upon removal and facilitate precise fit of subsequent stage scaffold module. A single or multiple hinge mechanism along nasal dorsum in the nasal implant is also contemplated that allows an initially low profile scaffold with the ability to project with or without a tissue expansion device. Further, incorporation of a patterned hinge facilitates accompanying a second stage module fit.

An accompanying tissue expansion mechanism allows for calculated projections with gradual expansion. The tissue may be expanded with expansion techniques, such as serial balloon injection or via an osmotic expansion device.

Composite material designs in accordance with certain aspects of the present disclosure allow for four dimensional conformational shape and projection with an initially low profile or flat implant gradually achieving desired shape. In certain aspects, the tissue scaffold component could have a low profile when implanted and gradually achieves nasal/nasal/etc. shape.

Prefabricated ancillary mechanisms may also be incorporated in scaffolds, for example, a Luer lock attachment allowing ease for hydrogel, solution, nanoparticle, growth factor, cell, tissue infusion. The tissue scaffold implant device may also have suction pathways formed therein to allow the scaffold to serve as its own suction port providing optimal soft tissue adherence and minimization of hematoma or seroma formation.

Thus, in certain aspects, the tissue scaffold component further comprises a drain port and an internal channel in fluid communication therewith.

In certain other aspects, the tissue scaffold component comprises at least one hollow feature configured to receive a tissue sample, such as a punch biopsy tissue.

In certain aspects, the tissue scaffold component further comprises a Luer lock in fluid communication with the plurality of pores.

In certain aspects, the plurality of open pores in the tissue scaffold component has a first pore density in a first region and a first rigidity level and a second pore density distinct from the first pore density in a second region having a second rigidity level.

Design and Manufacturing: Scaffold design begins with an anatomic based image. In particular, using a micro-CT with resolution of 2.5 µm, a high resolution DICOM file was produced. Segmentation of this scan was done in a Computer Aided Design (CAD) Software Suite, Mimics and 3-Matic, to model the scan in three dimensions (Materialise, Plymouth Mich., US). The model was further designed for symmetry and incorporation of cartilage inset sites amenable to precise placement of hole punch biopsy locations through Boolean subtraction techniques. Anatomical landmarks key for surgical implantation such as septal cartilage and major alar cartilage were preserved in the model. The 3D nasal cartilage model was printed out of polycaprolactone (PCL) creating a biocompatible, bioabsorbable nasal scaffold.

Scaffold-to-Skin Contact Analysis: A skin overlay for the nose bioscaffold was developed in CAD. Nonlinear contact analysis was performed utilizing the FEBio software suite to simulate the contact between the skin flap on the nose scaffold as the skin flap is pulled over the nose.

Cadaveric Implantation: The nasal scaffold was surgically implanted into an elderly male fresh human cadaver to demonstrate its functionality and efficacy. Both the open septorhinoplasty approach and total nasal defect and reconstruction utilizing a forehead flap for soft tissue coverage and pericranial flap for internal mucosal lining were tested.

The additive manufacturing process successfully 3D prints the nasal cartilage tissue engineering scaffold. Measurements taken from the cadaveric cartilage, 3D CAD model, and final 3D printed scaffold demonstrate accuracy of the scaffold.

FIGS. 1A-1D show scaffold-to-skin contact analysis results for the nose. The scaffold included a cylinder of skin around the nose scaffold that is formed of PCL with a Young's modulus (E)=250 MPa. The following parameters were used: skin nonlinear elastic (Fergold): Ogden c1=0.11 MPa; c2=8.3. Nonlinear Contact Analysis is conducted to simulate contact between skin flap on nose scaffold as skin flap is pulled over nose. For skin, 14,720 Hex8 elements and 19695 nodes are used. For nose, 29,583 Tet10 elements, 51717 nodes are used. The analysis ran to 1.5 mm displacement before convergence failure (first run).

Figures 1A, 1B, 1C, 1D:
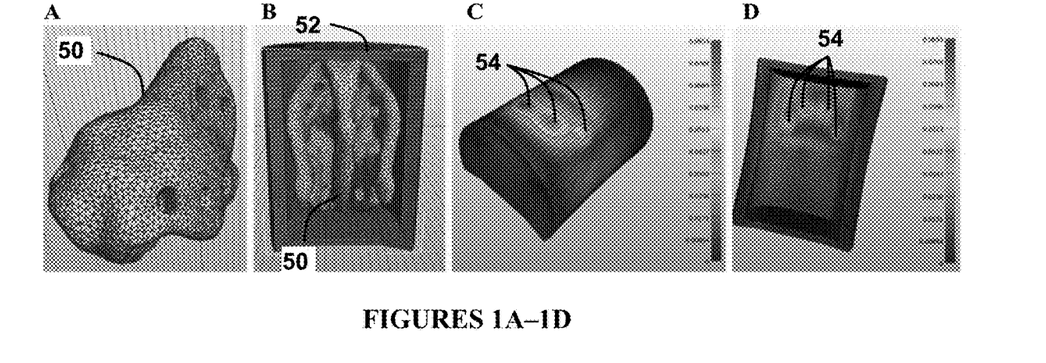
FIG. 1A shows finite element mesh of nose scaffold (yellow).
FIG. 1B shows finite element mesh of nose scaffold (yellow) inside simulated skin flap (purple). Nose scaffold alone showing dome defining points that cause high contact strains.
FIGS. 1C and 1D show large strains (~8%) on outside of skin over scaffold protuberances.

FIGS. 1A-1B show a finite element mesh of nose scaffold 50 (yellow) inside simulated skin flap 52 (purple). FIGS. 1C-1D show a nasal scaffold alone showing dome defining points that cause high contact strains. Large strains (approximately 8%) occur on the outside of skin over scaffold protuberances as shown in FIGS. 1C-1D. The highest stress areas 54, representing dome defining points, on the nasal scaffold were revealed on the simulated skin flap. Strains in the skin flap demonstrated a nasally double efficacy in strain levels than those on the bottom of the skin flap. The strains were lower at the contact points than on the outside of the skin flap due to the bending deformation of the simulated skin.

Figures 2A, 2B:
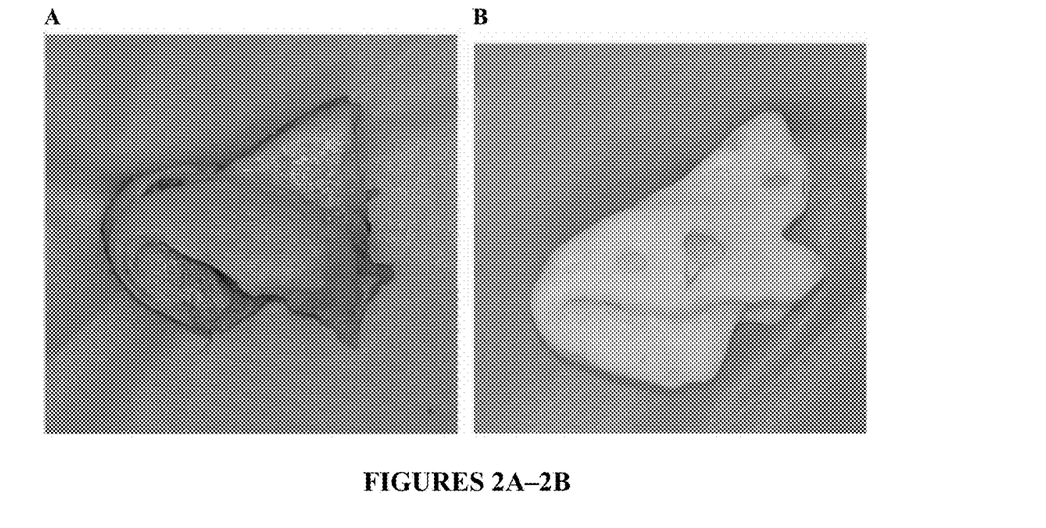
FIG. 2A shows a patient nose with MicroCT scan demonstrating anatomic based design. More specifically, a human nasal tripod including subperichondrial dissection of the upper and lower lateral cartilages, septal cartilage, and intracartilaginous ligaments is shown.
FIG. 2B shows a GMP manufactured, laser sintered polycaprolactone (PCL) bioscaffold produced based on CAD generated tissue scaffold having predesigned holes for cartilage placement/suture.

FIGS. 2A-2B show an anatomic based total nasal bioscaffold design. FIG. 2A shows a patient nose with MicroCT scan demonstrating anatomic based design. More specifically, a human nasal tripod including subperichondrial dissection of the upper and lower lateral cartilages, septal cartilage, and intracartilaginous ligaments is shown. FIG. 2B shows a GMP manufactured, laser sintered polycaprolactone (PCL) bioscaffold produced based on CAD generated tissue scaffold having predesigned holes for cartilage placement and/or suture holes. Non-porous and porous scaffolds can be produced.

Figures 3A, 3B, 3C, 3D, 3E, 3F, 3G, 3H:
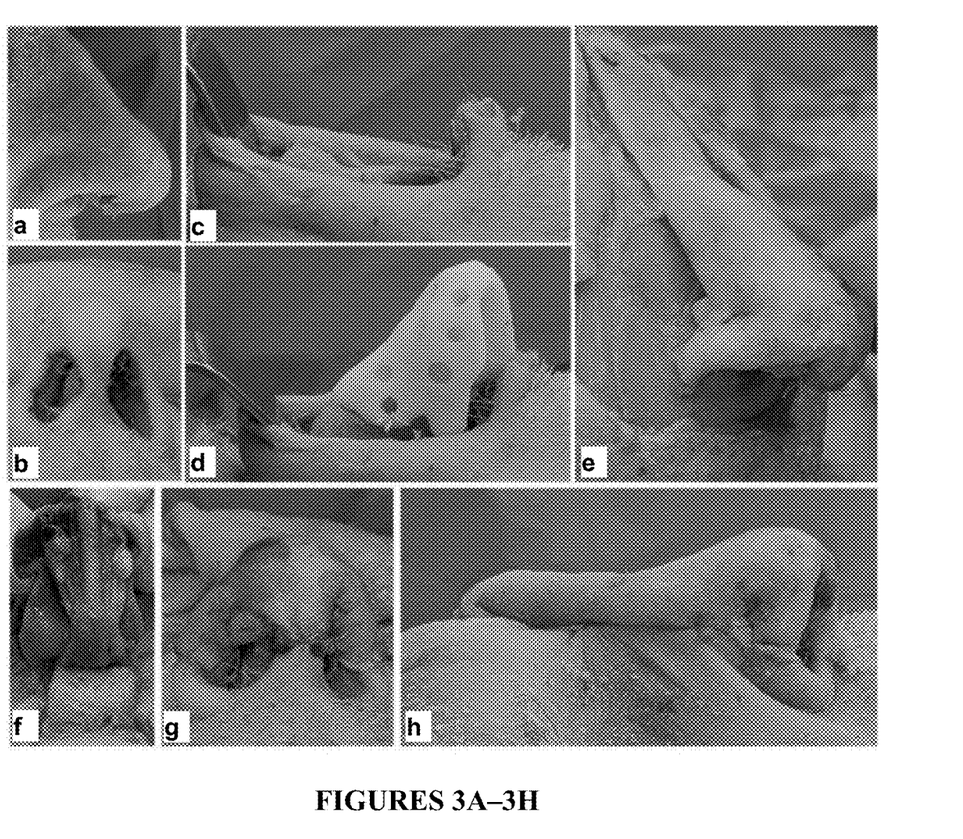
Figure 4A:
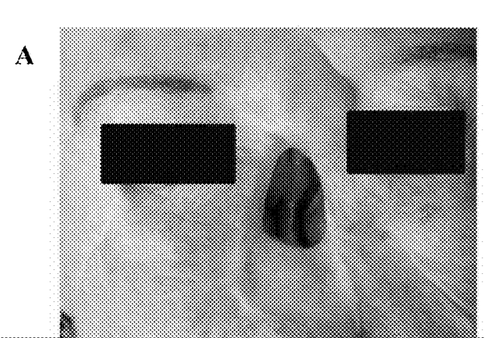
FIG. 4A shows a subject in need of a total nasal bioscaffold. A MicroCT scan was performed to determine the appropriate anatomical structure for a nasal bioscaffold for the patient.
Figure 4B:
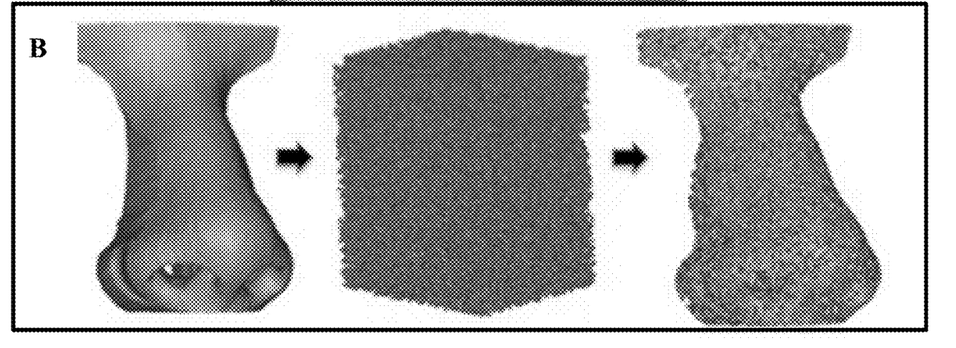
FIG. 4B shows a computer rendered anatomical-based model of the subject's nasal implant and the computer rendered anatomical-based model of the porous scaffold.
Figure 4C:
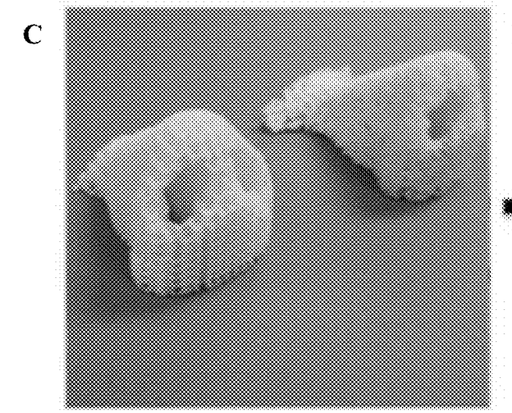
FIG. 4C shows a 3D printed total nasal bioscaffold.
Figure 4D:
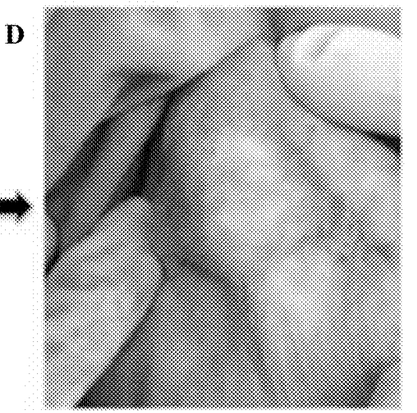
FIG. 4D shows the subject and the 3D printed total nasal bioscaffold following implantation.

Human Cadaveric Rhinoplasty (Cadaveric Prelaminated Forehead Flap, Pericranial Flap) Outcomes: The nasal cartilage tissue engineering scaffold was surgically implanted in a cadaver to demonstrate aesthetics (FIGS. 3A-3H). An open rhinoplasty exposed the cadaveric cartilage (FIGS. 3A-3C). Fresh human cadaveric implantation of the 3D printed nasal scaffold was placed using a forehead flap for overlying soft tissue coverage and a pericranial flap for internal mucasal lining (FIG. 3D). After forehead flap elevation, total nasal bioscaffold incorporation, and pericranial flap mucosal lining placement, the prelaminated total nasal graft was rotated over the total nasal defect. FIGS. 3D-3E. After removing the cadaveric cartilage, the nasal cartilage tissue engineering model was implanted and covered in skin (FIG. 3F-3H). Comparing before and after, the scaffold was able to withstand the placement and correct the dorsal hump.

Excellent integration into the residual nasal piriform, vomer, and adjacent soft tissue was appreciated. The entire procedure was performed in approximately 60 minutes and would require a brief second procedure to divide and inset the nasal forehead pedicle.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. A nasal tissue implant for reconstruction of nasal tissue in a subject, the implant comprising:
a tissue scaffold component comprising a biocompatible polymeric material having a plurality of open pores including a plurality of first open pores having a first average diameter and a plurality of second open pores having a second average diameter distinct from the first average diameter and distributed throughout the body of the tissue scaffold component, wherein:
the first average diameter is greater than or equal to about 1 mm and less than or equal to about 10 mm,
the plurality of first open pores includes at least one first open pore that is configured to receive a punch biopsy tissue insert and is positioned to correspond to one or more stress points with adjacent skin when implanted in the subject, wherein at least one of the one or more stress points correspond to a nasal tip defining regions delineated by the intermediate crura of the lower lateral cartilages and the nasal dorsum and the plurality of second open pores is configured to support cell growth, and the tissue scaffold component conforms to a portion of the subject's nasal region and defines at least a portion of the subject's nasal anatomy.

2. The nasal tissue implant of claim 1, wherein the second average diameter is greater than or equal to about 0.05 mm to less than or equal to about 2 mm.

3. The nasal tissue implant of claim 1, wherein the biocompatible polymeric material comprises a biodegradable polymer.

4. The nasal tissue implant of claim 1, wherein the biocompatible polymeric material comprises polycaprolactone.

5. The nasal tissue implant of claim 1, wherein the biocompatible polymeric material further comprises a bioactive agent selected from the group consisting of: a cell adhesion factor, a growth factor, a peptide, a cytokine, a hormone, a pharmaceutical active, and combinations thereof.

6. The nasal tissue implant of claim 1, further comprising a biomaterial selected from the group consisting of: an isolated tissue material, a hydrogel, acellularized dermis, an acellularized tissue matrix, a composite of acellularized dermis matrix and designed polymer, or a composite of acellularized tissue matrix and designed polymer, and combinations thereof.

7. The nasal tissue implant of claim 1, further comprising a material selected from the group consisting of: nanoparticles, growth factors, cells, tissue infusions, and combinations thereof.

8. The nasal tissue implant of claim 1, wherein at least a portion of the plurality of open pores is in fluid communication with one another and configured to receive a fluid.

9. The nasal tissue implant of claim 1, wherein the tissue scaffold component has a first pore density in a first region and a first rigidity level and a second pore density distinct from the first pore density in a second region having a second rigidity level.

10. A method of making an implantable nasal tissue implant for reconstructing a portion of a nasal anatomy of a human or other animal subject comprising:
    laser sintering or three-dimensional (3D) printing a biocompatible polymeric material to form a tissue scaffold component comprising a biocompatible polymeric material having a plurality of open pores including a plurality of first open pores having a first average diameter and a plurality of second open pores having a second average diameter distinct from the first average diameter and that is configured to support cell growth and distributed throughout the body of the tissue scaffold, wherein the first average diameter is greater than 1 mm and less than or equal to about 10 mm, and the plurality of first open pores includes at least one first open pore that is configured to receive a punch biopsy tissue insert and is positioned to correspond to one or more stress points with adjacent skin when implanted in the human or other animal subject, wherein at least one of the one or more stress points correspond to a nasal tip defining regions delineated by the intermediate crura of the lower lateral cartilages and the nasal dorsum, and wherein the tissue scaffold component substantially conforms to a nasal region specific to the human or other animal subject.

11. The method of claim 10, further comprising designing a tissue scaffold component from a set of medical image data of the nasal region specific to the human or other animal subject prior to the laser sintering or three-dimensional (3D) printing.

12. The nasal tissue implant of claim 1, wherein a portion of the first plurality of open pores is further configured to receive at least one suture configured to secure the nasal tissue implant to native tissue in the subject's nasal region.

13. A nasal tissue implant for reconstruction of nasal tissue in a subject, the implant comprising:
    a tissue scaffold component comprising a biocompatible polymeric material having a plurality of open pores configured to support cell growth and distributed throughout the body of the tissue scaffold component, and at least one hollow feature configured to receive a punch biopsy tissue insert having an average diameter of greater than or equal to about 1 mm and less than or equal to about 10 mm that is positioned at stress points with adjacent skin when implanted in the subject, wherein at least a portion of the stress points correspond to nasal tip defining regions delineated by the intermediate crura of the lower lateral cartilages and the nasal dorsum, wherein the at least one hollow feature is in fluid communication with the plurality of open pores and the tissue scaffold component conforms to a portion of the subject's nasal region and defines at least a portion of the subject's nasal anatomy.

14. The nasal tissue implant of claim 13, wherein the biocompatible polymeric material comprises polycaprolactone.

15. The nasal tissue implant of claim 13, wherein the biocompatible polymeric material further comprises a bioactive agent selected from the group consisting of: a cell adhesion factor, a growth factor, a peptide, a cytokine, a hormone, a pharmaceutical active, and combinations thereof.

16. The nasal tissue implant of claim 13, further comprising a biomaterial selected from the group consisting of: an isolated tissue material, a hydrogel, acellularized dermis, an acellularized tissue matrix, a composite of acellularized dermis matrix and designed polymer, or a composite of acellularized tissue matrix and designed polymer, and combinations thereof.

17. The nasal tissue implant of claim 13, further comprising a material selected from the group consisting of: nanoparticles, growth factors, cells, tissue infusions, and combinations thereof.

18. The nasal tissue implant of claim 13, wherein the plurality of open pores in the tissue scaffold component has a first pore density in a first region and a first rigidity level and a second pore density distinct from the first pore density in a second region having a second rigidity level.

19. The nasal tissue implant of claim 13, wherein the plurality of open pores has an average diameter of greater than or equal to about 0.05 mm to less than or equal to about 2 mm.

20. The nasal tissue implant of claim 13, wherein the nasal tissue implant further comprises at least one hollow feature configured to receive at least one suture positioned to secure the nasal tissue implant to native tissue in the subject's nasal region.

* * * * *